(12) United States Patent
Nakanishi et al.

(10) Patent No.: US 9,521,981 B2
(45) Date of Patent: Dec. 20, 2016

(54) X-RAY CT SYSTEM

(71) Applicant: TOSHIBA MEDICAL SYSTEMS CORPORATION, Otawara-Shi (JP)

(72) Inventors: Satoru Nakanishi, Utsunomiya (JP); Tatsuro Suzuki, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 145 days.

(21) Appl. No.: 14/240,655

(22) PCT Filed: Apr. 11, 2013

(86) PCT No.: PCT/JP2013/060973
§ 371 (c)(1),
(2) Date: Feb. 24, 2014

(87) PCT Pub. No.: WO2013/154167
PCT Pub. Date: Oct. 17, 2013

(65) Prior Publication Data
US 2014/0169521 A1   Jun. 19, 2014

(30) Foreign Application Priority Data
Apr. 11, 2012 (JP) ................... 2012-090362

(51) Int. Cl.
*A61B 6/03* (2006.01)
*A61B 6/04* (2006.01)
(Continued)

(52) U.S. Cl.
CPC ............... *A61B 6/035* (2013.01); *A61B 6/032* (2013.01); *A61B 6/0457* (2013.01); *A61B 6/06* (2013.01); *A61B 6/54* (2013.01)

(58) Field of Classification Search
CPC ........... A61B 6/035; A61B 6/032; A61B 6/06; A61B 6/0457; A61B 6/54
See application file for complete search history.

(56) References Cited

U.S. PATENT DOCUMENTS 5,412,562 A   5/1995  Nambu et al.
7,313,216 B2 * 12/2007  Nishide ................. A61B 6/032
                                              378/15
(Continued)

FOREIGN PATENT DOCUMENTS

CN   1448112 A    10/2003
CN   101401727 A   4/2009
(Continued)

OTHER PUBLICATIONS

International Search Report Issued May 21, 2013 in PCT/JP13/060973 Filed Apr. 11, 2013.
(Continued)

*Primary Examiner* — Wyatt Stoffa
*Assistant Examiner* — Sean Luck
(74) *Attorney, Agent, or Firm* — Oblon, McClelland, Maier & Neustadt, L.L.P.

(57) ABSTRACT

X-ray CT system is provided that reduces waiting time for shuttle scanning, comprising: top-plate moving unit; rotary moving unit; data acquisition system; and control unit. Top-plate moving unit displaces top plate to reciprocate in a direction from a starting point to an ending point and in the direction from the ending point to the starting point. Rotary moving unit drives X-ray radiator radiating X-rays to revolve around the subject. Data acquisition system detects X-rays passed through the subject and to gather projection data. Controller controls at least top-plate moving unit so that, during a scanning with X-rays, while projection data are gathered with reciprocating movement of top plate between the starting point and the ending point and with X-ray radiator being driven to make revolving movement, the duration required for reciprocation of the top plate movement being an integral multiple of revolution period of the revolving movement of X-ray radiator.

19 Claims, 5 Drawing Sheets

(51) Int. Cl.
  *A61B 6/06* (2006.01)
  *A61B 6/00* (2006.01)

(56) References Cited

U.S. PATENT DOCUMENTS

| | | |
|---|---|---|
| 7,522,696 B2 | 4/2009 | Imai |
| 7,606,345 B2 | 10/2009 | Nishide et al. |
| 7,774,040 B1* | 8/2010 | Dutta ..................... A61B 6/032 378/15 |
| 8,320,520 B2 | 11/2012 | Kondo |
| 2010/0027736 A1* | 2/2010 | Bruder ................. A61B 5/0456 378/8 |

FOREIGN PATENT DOCUMENTS

| | | |
|---|---|---|
| CN | 201498132 U | 6/2010 |
| CN | 103237498 A | 8/2013 |
| JP | 5 309089 | 11/1993 |
| JP | 6 78916 | 3/1994 |
| JP | 6 125889 | 5/1994 |
| JP | 2007 275314 | 10/2007 |
| JP | 2008 119381 | 5/2008 |
| JP | 2009 89760 | 4/2009 |
| JP | 2011 62445 | 3/2011 |

OTHER PUBLICATIONS

Combined Office Action and Search Report issued Aug. 25, 2015 in Chinese Patent Application No. 201380003639.9 (with English translation of categories of documents).

\* cited by examiner

| SCANNING RANGE [mm] |
|---|
| 10 |
| 15 |
| ⋮ |
| 45 |
| 50 |

X-RAY CT SYSTEM

TECHNICAL FIELD

Embodiments according to the present invention relate to X-ray CT systems.

BACKGROUND ART

X-ray CT systems irradiate the subject with X-rays and acquire image data (hereinafter referred to merely as "data") that represent a view in a predetermined sectional plane of the subject, on the basis of the X-rays that have passed through the subject.

An example of a method of X-ray irradiation is involved in shuttle scanning, where the X-ray CT system performs scanning while the top plate with the subject is being reciprocated between the starting point and the ending point of a set scanning range (e.g., patent reference 1).

There is a case where a scanning duration is set for the X-ray CT system, where the scanning duration is a time that the top plate takes to make a reciprocating movement in connection with X-ray irradiation. The scanning duration includes an acceleration time, a constant-speed time, and a deceleration time, along with a waiting time (interval), during which the top plate is stationary. Incidentally, the acceleration time is the time when the top plate is being translated by the X-ray CT system in accelerating mode; the constant-speed time is the time when the top plate is being translated at a constant speed by the X-ray CT system; and the deceleration time is the time when the top plate is being translated by the X-ray CT system in decelerating mode. In addition, during the waiting time, the X-ray CT system performs such actions as offset correction on the data, directional switching of the top plate, input and output of control signals, tracking agreement (described later), measurement of the load that is caused by the subject.

If an ADCT (Area Detector CT) is applied to the X-ray CT system, then dynamic scanning is possible in which a certain scanning range is being scanned at once. However, even without the application of an ADCT, pseudo-dynamic scanning can be accomplished by the use of shuttle scanning. Shuttle scanning in this case is used mainly for observation of chronological changes in the subject.

In this type of shuttle scanning, data are acquired during the time s of the movement of the top plate from the starting point to the ending point of the scanning range, and data are also acquired during the time t of the movement from the ending point to the starting point. Furthermore, in the shuttle scanning, differential images are generated from the data sets that have been acquired respectively during the corresponding different times of the movement, for observation of chronological changes. For observing chronological changes by using differential images, therefore, it is important that the differences between the respective data sets be accurately captured for the corresponding different movements, for example, during the movement times s, t.

In such dynamic scanning as done with the ADCT, data are acquired in a lump for a predetermined range of the subject, and the circular orbit taken for the scanning is uniform even at different time points. By contrast, in the shuttle scanning, generally, the scanning tracks are different for the data set acquired during movement time s and for the data set acquired during movement time t. For example, when the scanning track is clockwise in the direction of the movement from the starting point to the ending point, the scanning track turns counterclockwise, i.e., in the direction of the movement from the ending point to the starting point. Because of this reason, the differential image that is created from the data sets achieved during movement time s and movement time t may include differences that result from factors other than chronological changes. Such differences, if any, adversely affect the algorithmic analysis that follows in the process.

For example, if differential processing is executed for two data sets that have been acquired for different scanning tracks, then the resultant differential image may include an artifact for one data set that has occurred during one scanning time and another artifact for the other data set that has occurred during the other scanning time. If the difference shown in the differential image is extremely small or is a little different in luminance from the part other than the differential, it is difficult for the examiner to distinguish between real differences and artifacts that have appeared in the differential image.

PRIOR ART REFERENCES

Patent References

[Patent Reference 1] Japanese Laid-Open Patent Publication No. 2007-275314.

SUMMARY OF THE INVENTION

Problems to be Solved by the Invention

The following two techniques are applied not to allow the appearance, in the differential image, of differences that result from factors other than chronological movements.

(1) The differences that have resulted from factors other than the chronological movements are removed by a process executed with software.

(2) Tracking movements are made to precisely agree for IN actions, i.e., the movements of the top plate in the direction from the starting point to the ending point within the scanning range. Tracking movements are made to precisely agree also for OUT actions, i.e., the movements of the top plate in the direction from the ending point to the starting point.

Here, attention is paid to technique (2). In this technique, the rotary mechanism is controlled on the side of the starting point of the repeated reciprocating movement of the top plate in the shuttle scanning so that tracking agreement is maintained for each scanning movement. In this case, it takes time to make precise tracking agreement, and therefore, it tends to make the waiting time longer.

Here, if the waiting time becomes longer, then the interval between the data acquisitions, which are executed while the top plate is being reciprocated, increases by the lengthened time of the waiting time. If the interval between the data acquisitions is longer, then, for example, the scanning period increases accordingly. Also, the longer the interval between the data acquisitions, the larger the radiation exposure. In addition, in cases where shuttle scanning is applied to analyses of blood flow (perfusion) in the capillary system, there is a problem that the lengthened interval between the data acquisitions can be a factor that affects the accuracy of the analysis done by using differential images.

The present embodiment is to solve the above-mentioned problem, and its objective is to provide an X-ray CT system that can reduce the waiting time for shuttle scanning.

Means for Solving the Problems

In order to solve above-mentioned problem, an X-ray CT system of this embodiment comprises: a top-plate moving unit; a rotary moving unit; a data acquisition system; and a control unit. The top-plate moving unit is configured to displace the top plate to reciprocate in a direction from a predetermined starting point to a predetermined ending point and in the direction from the ending point to the starting point. The rotary moving unit is configured to drive an X-ray radiator, which radiates X-rays, to revolve around the subject. The data acquisition system is configured to detect X-rays that have passed through the subject and to gather projection data. The control unit is configured to control at least the top-plate moving unit in such a way that, during a scanning with X-rays, while the projection data are gathered with the top plate being driven to make one reciprocating movement between the starting point and the ending point and with the X-ray radiator being driven to make revolving movement, the duration required for the top plate to make one reciprocating movement is made an integral multiple of the revolution period of the revolving movement of the X-ray radiator.

PREFERRED EMBODIMENTS OF THE INVENTION

Figure 1:
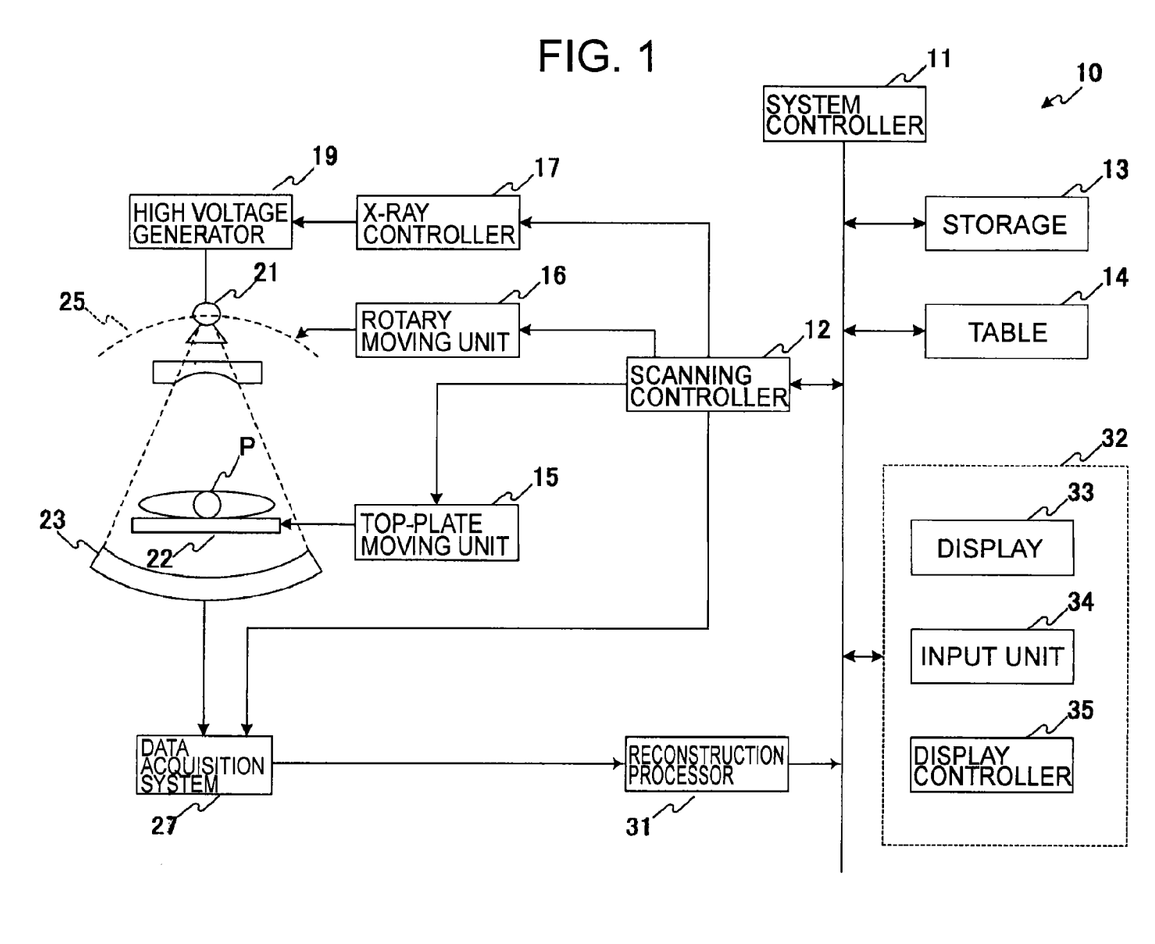
FIG. 1 is a block diagram showing the configuration of an X-ray CT system as an embodiment.

An embodiment of X-ray CT system is described with reference to each of the drawings.
[Configuration]
The configuration of the X-ray CT system is briefly explained in reference to FIG. 1, which is a block diagram showing the configuration of the X-ray CT system.

The X-ray CT system 10 comprises a system controller 11, a scanning controller 12, a storage 13, a table 14, a top-plate moving unit 15, a rotary moving unit 16, an X-ray controller 17, a high voltage generator 19, an X-ray radiator 21, a top plate 22, an X-ray detector 23, a rotary mechanism 25, a data acquisition system 27, a reconstruction processor 31, and an interface 32.

The system controller 11 comprises a central processing unit (CPU), and so on, and the system controller 11 controls and unifies the scanning controller 12, the storage 13, the table 14, the reconstruction processor 31, and the interface 32. Incidentally, one of the system controller 11, the scanning controller 12, and the display controller 35 or two of them as a combination are an example of the control unit that is described later.

The scanning controller 12 outputs control signals in accordance with the image-capturing conditions that are set up for scanning the subject P, and the control signals are sent, respectively, to the top-plate moving unit 15, to the rotary moving unit 16, to the X-ray controller 17, to the high voltage generator 19, to the X-ray radiator 21, to the X-ray detector 23, to the rotary mechanism 25, and to the data acquisition system 27. The data acquisition system 27 is an example of the "data acquisition system" that is mentioned in the claims.

Here, the image-capturing conditions include conditions for helical shuttle scanning on the movement of the top plate 22, which is reciprocated in the direction from a predetermined starting point to a predetermined ending point and in the direction from the ending point to the starting point while the X-ray radiator 21 is being driven in revolving motion. In addition, the image-capturing conditions include a scanning range and a revolution period for a helical shuttle scanning in order to gather projection data while the top plate 22 is being reciprocated. The scanning range is the distance from the starting point to the ending point. The revolution period is a period for the revolution of the X-ray radiator 21. Incidentally, helical shuttle scanning may be hereinafter referred to simply as "scanning".

The scanning range (the starting point and the ending point) is set up through the interface 32 by the user while the revolution period represents a time required for the X-ray radiator 21 to make one revolution [sec/rot]. The revolution period is set up with an initial value, or may be set up through the interface 32 by the user.

Figure 2:
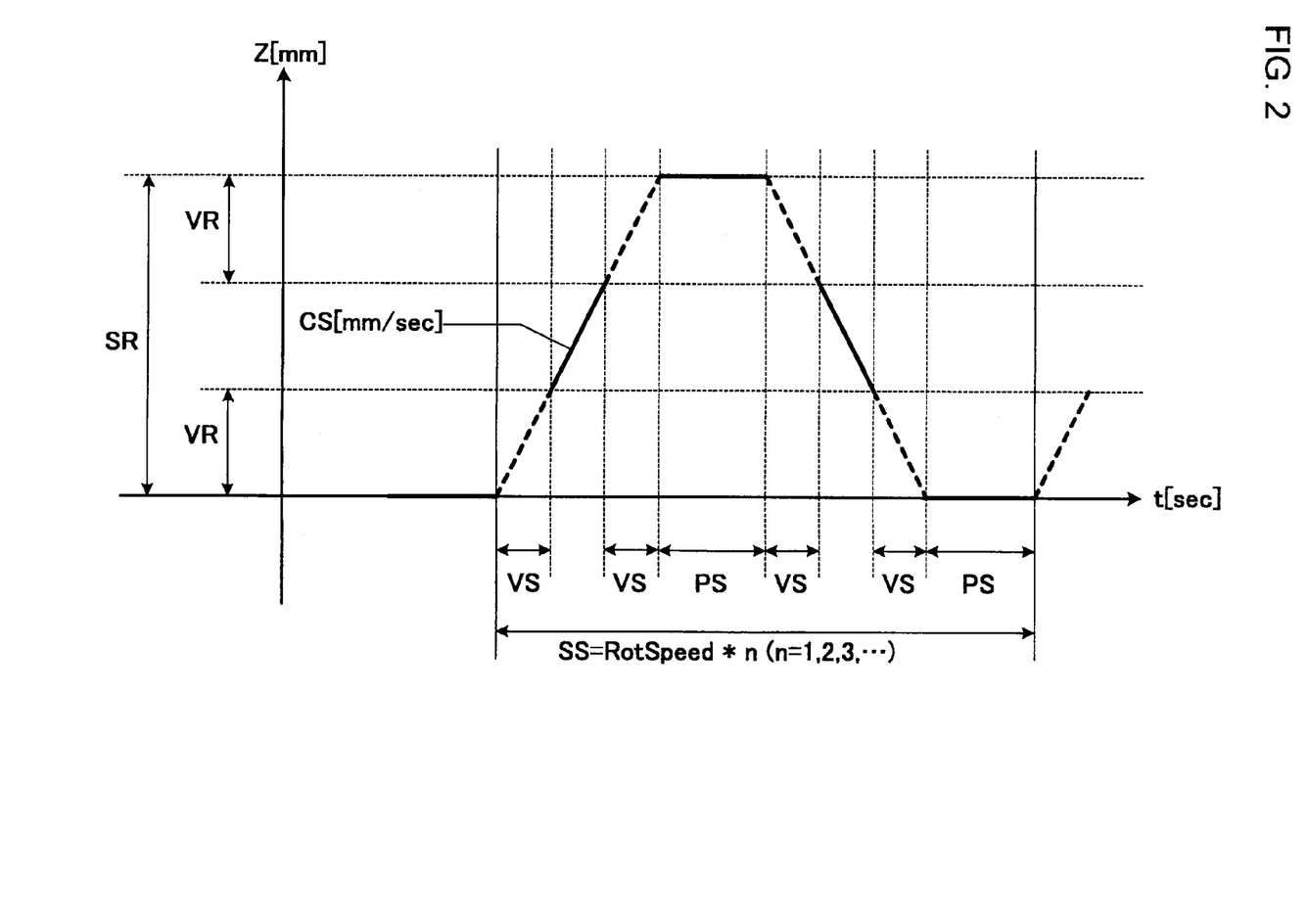
FIG. 2 is a diagram showing relations between a scanning range and a duration for the top plate to make a back-and-forth movement.

FIG. 2 is a drawing showing relations between the duration and the scanning range (distance) for one reciprocating movement of the top plate 22. In FIG. 2, the duration t [sec] is shown along the horizontal axis while the scanning range [mm] is shown along the vertical axis. In addition, in FIG. 2, the duration is designated with "SS". Incidentally, the duration may be hereinafter referred to also as "scanning duration". Also, in FIG. 2, the scanning range is designated with "SR".

When the top plate 22 is moved from the starting point to the ending point, the movement of the top plate 22 is, at first, accelerated, then, changed from the acceleration to a constant speed, and then decelerated from the constant speed. Likewise, the movement from the ending point to the starting point is carried out in the same way. In FIG. 2, dashed lines indicate the area representing the acceleration (acceleration area), where the movement of the top plate 22 is accelerated, and the area representing the deceleration (deceleration area), where the movement of the top plate 22 is decelerated. In addition, solid lines indicate the area representing the constant speed (constant speed area), where the movement of the top plate 22 is at constant speed.

The duration SS, therefore, includes the acceleration time, the constant-speed time, and the deceleration time. Incidentally, the acceleration time is the time during which the X-ray CT system accelerates the top plate; the constant speed time is the time during which the X-ray CT system moves the top plate at a constant speed; and the deceleration time is the time during which the X-ray CT system decelerates the top plate. In FIG. 2, the acceleration time and the deceleration time are designated with "VS", and the acceleration area and the deceleration area are designated with "VR". Incidentally, the acceleration time may be the same as the deceleration time, or they may be different. Also, the acceleration area may be the same as the deceleration area, or they may be different.

In addition, the duration SS includes a waiting time (interval). The waiting time is the time during which the top plate 22 is stopped after it has been moved from the starting point to the ending point and before it is to be moved from the ending point to the starting point. In FIG. 2, the waiting time is designated with "PS". Furthermore, the duration SS includes another waiting time PS, which is the time before the restart of the reciprocating movement of the top plate 22 after it has been moved from the ending point to the starting point. This waiting time PS for starting another reciprocating movement is the waiting time PS before the top plate 22 is being moved from the starting point to the ending point. Incidentally, these waiting times PS may be the same, or they may be different. The term "waiting time PS" in the following discussion means at least one of the time between the forward movement and the backward movement of the top plate 22 and the time between the backward movement and the forward movement.

The constant speed area, which is the range where the top plate 22 is moved at constant speed, is the subtraction of the acceleration area VR and the deceleration area VR from the scanning range SR. (CR=SR−2×VR). Incidentally, "CR" represents the constant speed area. The constant speed time is, therefore, expressed as the following expression (1) with the scanning range SR and the acceleration area VR.

$$\text{Constant speed time} = (SR - 2 \times VR)/CS \quad (1)$$

Here, "CS" represents the top-plate traveling velocity [mm/sec], at which the top plate 22 travels in the constant speed area. Incidentally, the top-plate traveling velocity in the constant speed area is determined as the lower of the upper limits of the following two factors: 1) reconstruct-ability condition, and 2) traveling velocity of the top plate.

The X-ray CT system in shuttle scanning moves the top plate 22 and, at the same time, makes the X-ray radiator 21 revolve so as to irradiate the subject with X-rays. X-rays having been radiated toward the subject, who is placed on the top plate 22, which is now moving, pass through the subject and are detected by the X-ray detector 23. Furthermore, the X-ray CT system executes reconstruction-processing on the X-rays that have been detected in this way. However, the reconstruction-processing may be affected by the top-plate traveling velocity. For example, the reconstruction-processing is accompanied with some kind of interpolation-processing. Since the higher the top-plate traveling velocity, the larger the range of interpolation that the system has to deal with, the spatial resolution of the image on the subject may be affected in the rostrocaudal direction. Depending on the reconstruction-processing capacity of the X-ray CT system, the time required for the reconstruction-processing can differ. As a result, the reconstruction-processing may not be able to cooperate with the top-plate traveling velocity. In other words, the condition for reconstruct-ability is the upper limit to the traveling velocity of the top plate 22, at which the X-ray CT system can execute reconstruction-processing in concert with the movement of the top plate 22.

The duration SS is the time that is the sum of the acceleration time VS, the constant speed time, the deceleration time VS, and the waiting time PS.

The duration SS is, therefore, expressed as the following expression (2).

$$SS = 4 \times VS + 2 \times PS + 2 \times (SR - 2 \times VR)/CS \quad (2)$$

The control unit receives the information of a scanning range set by the user. The control unit controls the top-plate moving unit 15 for this scanning range. In this control, the duration for the top plate 22 to be driven for one reciprocating movement is determined as an integral multiple of the revolution period of the X-ray radiator 21. As a result, in the shuttle scanning, it is not necessary that the waiting time include a time for making precise tracking agreement for the top plate 22 that has made one reciprocating movement and is to start another reciprocating movement. In other words, in the above-described shuttle scanning, for differential images to be generated between the data sets achieved for the IN actions, even though no time is allocated for making precise tracking agreement between the IN actions, there is always tracking agreement between the successive IN actions. Otherwise, such time allocation is necessary and be included between the OUT action and the immediately following IN action. Likewise, when differential images are generated between the data sets achieved for the OUT actions in the shuttle scanning, even though no time is intentionally secured for making precise tracking agreement, there is always tracking agreement between the successive OUT actions.

According to this configuration, the duration for the top plate 22 to make one reciprocating movement can be made shorter, and the interval of data acquisition that corresponds to each of the reciprocating movements can be shortened accordingly. As a result, it is possible to make a reduction in radiation dose. In addition, because of the resultant shortened scanning period, the interval between the IN actions, for which differentiation is made, also becomes shorter. Likewise, the interval between the OUT actions, for which differentiation is made, also becomes shorter. Thus, there can be an improvement in the accuracy of the analysis that is done by using the differential images.

Incidentally, in the duration for the top plate 22 to make one reciprocating movement, the acceleration time VS, the deceleration time VS, and the waiting time PS are determined in advance. In other words, the value for each of these times is fixed until it is intentionally changed, i.e., a set-up change. For example, the duration is determined by adjusting the constant speed time, which is the time assigned for the top plate 22 to be moved at constant speed, or the duration is determined by adjusting the distance (constant speed area) over which the top plate 22 is to be moved at constant speed.

The control unit controls the top-plate moving unit 15 so that the duration for the top plate 22 to make one reciprocating movement is an integral multiple of the revolution period of the X-ray radiator 21.

(Method of Making the Duration an Integral Multiple of the Revolution Period)

Now, the description concerns a method of making the duration an integral multiple of the revolution period of the X-ray radiator 21.

An example in which the duration SS is made an integral multiple of the revolution period RS is shown as the following expression (3). Incidentally, the revolution period is represented by "RS", and the constant speed area is represented by "CR" in the following expression.

$$(4 \times VS + 2 \times PS + 2 \times CR/CS) = RS \times n (n=1,2,\ldots) \quad (3)$$

If the acceleration time VS, the deceleration time VS, and the waiting time PS are fixed, then the constant speed area CR is expressed as the following expression (4).

$$CR = (RS \times n - 4 \times VS - 2 \times PS) \times CS/2 \quad (4)$$

From the above expression (4), the scanning range SR is expressed as the following expression (5).

$$SR = 2 \times VR + CR = 2 \times VR + (RS \times n - 4 \times VS - 2 \times PS) \times CS/2 \quad (5)$$

The following can be said from the above expression (5).

In the setting up of the scanning range SR [mm], the scanning range SR is set not as a serial value, but as a value selected from a plurality of discrete values that correspond to integers n.

Incidentally, if the constraint of an "integral multiple of the revolution period" is removed, then the scanning range SR [mm] is set as a serial value. In that case, however, it is necessary to adjust the waiting time PS for tracking agreement. As a result, the duration for the top plate 22 to make one reciprocating movement increases, thus leading to, for example, an increase in radiation dose. Furthermore, this increased duration, in turn, lengthens the interval of the data acquisition that corresponds to each of the reciprocating movements. This can result in a decrease in the accuracy of the analysis conducted by using the differential images.

In contrast, the arrangement of discretely selecting the scanning range SR as this embodiment can shorten the scanning period for data acquisition for a given scanning range SR. As a result, a reduction can be made in radiation dose. In addition, for the resultant shuttle scanning, the interval of the data acquisition can be shortened between the IN actions and between the OUT actions. This can result in an improvement in the accuracy of the analysis conducted by using differential images.

As mentioned previously, the scanning range SRn takes a discrete value that depends on the value of the integer n. The scanning range SR may be, therefore, predetermined for some integers n (=1, 2, . . . ).

The storage 13 stores in advance a plurality of scanning ranges SR for which the duration for the top plate 22 to make one reciprocating movement SS is an integral multiple of the revolution period RS of the X-ray radiator 21.

In addition, the acceleration time VS, the constant speed time, the deceleration time VS, and the waiting time PS are memorized on the table 14 for each of the scanning ranges SR. The constant speed time is determined by, for example, expression (1).

In the above-mentioned arrangement, the scanning range SR is determined, for example, as follows. At first, a temporary scanning range is input by the user. The scanning range may be set up by the user inputting the starting point and the ending point for a scanning range. Alternatively, not limiting the arrangement to the input of the starting point and the ending point, simply, numerical information (for example, a length, etc.) may be input as a temporary scanning range. The control unit, upon receiving the temporary scanning range input, compares this scanning range (the length from the starting point to the ending point) with the scanning ranges SR (lengths) that are stored in the storage 13. The control unit, then, calculates one or two scanning ranges SR as selectable candidates, which are scanning ranges near to the temporary scanning range. Furthermore, the control unit executes display control to show the selectable candidates for the scanning range SR. In response to the user's operation selecting a scanning range SR from the selectable candidates, the control unit accepts the scanning range SR that has selected by the user, and applies it to the following control. Incidentally, if the control unit should calculate one selectable candidate that is the closest to the temporary scanning range, then it executes display control to show the selectable candidate that is the larger of the nearest scanning ranges, in comparison to the temporary scanning range.

Then, the control unit calculates, based on the selected scanning range SR, the acceleration time VS, the constant speed time (determined by expression (1)), the deceleration time VS, and the waiting time PS by using the table 14. The control unit then controls the top-plate moving unit 15, the rotary moving unit 16, the X-ray controller 17, the high voltage generator 19, the X-ray radiator 21, the X-ray detector 23, the rotary mechanism 25, and the data acquisition system 27, by applying these times, which have been calculated. Incidentally, the control unit may control at least one of the top-plate moving unit 15 and the X-ray radiator 21, based on the acceleration time VS, the constant speed time, the deceleration time VS, and the waiting time PS, which have been calculated.

Now, the configuration to execute the above-mentioned method is briefly described with reference to FIG. 1.

The top-plate moving unit 15 receiving control signals from the system controller 11 drives the top plate 22 to reciprocate in the rostrocaudal direction of the subject P. In other words, the top-plate moving unit 15 moves the top plate 22 in the direction from a predetermined starting point to a predetermined ending point and in the other way around from the ending point to the starting point.

The rotary moving unit 16 receiving control signals from the system controller 11 drives the rotary mechanism 25 to rotate.

The X-ray controller 17 controls the timing of the high voltage generation by the high voltage generator 19, based on control signals for X-ray beam generation, which are output from the system controller 11. The high voltage generator 19 supplies the X-ray radiator 21 with high voltages to generate X-ray beams in accordance with the control signals from the X-ray controller 17.

The X-ray radiator 21, upon receiving a high voltage, which is supplied from the high voltage generator 19, radiates a flabellate X-ray beam to the subject P. This X-ray beam has a thickness in the slicing direction. The X-ray detector 23 detects the X-ray beam that has radiated from the X-ray radiator 21 and have passed through the subject P.

The X-ray detector 23 has a plurality of channels of detector elements, which are disposed in an arc form around the focal point of the X-ray radiator 21.

The rotary mechanism 25 retains the X-ray radiator 21 and the X-ray detector 23 capable of revolving around the body axis of the subject P.

The data acquisition system 27 gathers projection data for a plurality of slices of the subject P, based on control signals for data acquisition, which are output from the system controller 11, and the acquisition system outputs the gathered data.

The reconstruction processor 31 simultaneously reconstructs a plurality of tomographic images of the subject P, based on the projection data for the slices of the subject P, which have been gathered by the data acquisition system 27. The display controller 35 displays, on a display 33, the tomographic images of the subject P that have been reconstructed.

The interface 32 comprises the display 33, an input unit 34, and the display controller 35, which controls the display 33.

The input unit 34 comprises a mouse, a keyboard, and so on, which are used for inputting various types of information.

The display controller 35 displays a plurality of scanning ranges, which are stored in the storage 13, selectable on the display 33.

Now, an outline of actions of the X-ray CT system is described in connection with the user's selection of a scanning range SR by using the interface 32 of the X-ray CT system of this embodiment, with reference to FIG. 3. At first, the user sets a duration SS for the top plate 22 to make one reciprocating movement as an integral multiple of the revolution period RS, through the interface 32. Then, the control unit of the X-ray CT system calculates a plurality of scanning ranges SR as selectable candidates, based on the duration SS. After that, the control unit accepts the information of a scanning range SR that has been selected from the scanning ranges SR by the user, who has performed selection operation. The following describes a specific example of a selection. Incidentally, the following discussion concerns another embodiment other than the above-mentioned "arrangement where a temporary scanning range is set".

Figure 3:
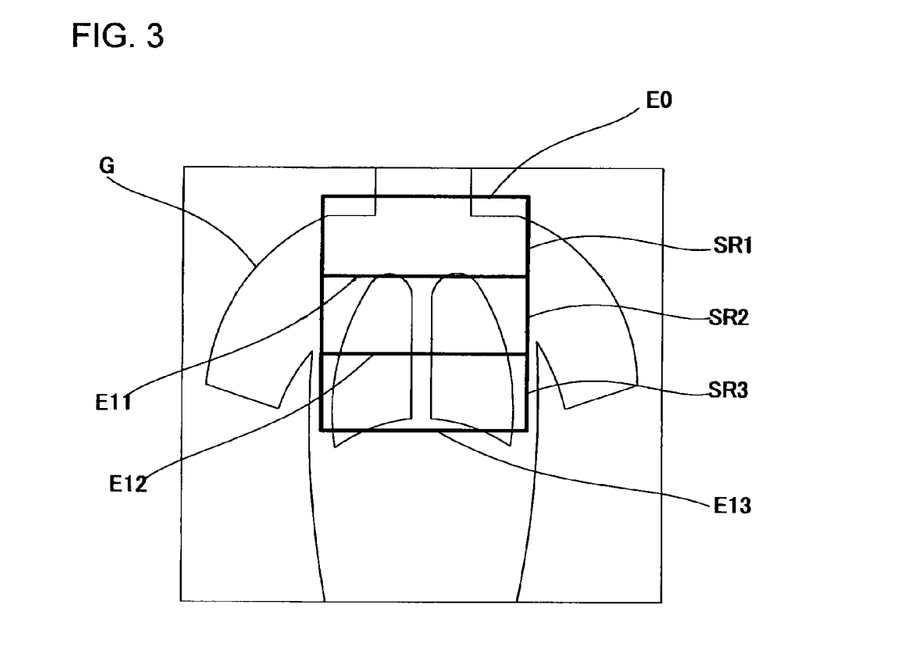
FIG. 3 is a drawing showing a plurality of scanning ranges that are indicated over a scanogram of the subject.

FIG. 3 is a drawing showing a plurality of scanning ranges that are indicated over a scanogram of the subject P. In FIG. 3, the scanogram is designated with "G" while a plurality of scanning ranges are designated with "SR1", "SR2", and "SR3". In addition, one end of each of the scanning ranges is designated with "E0" while the opposite end of each of the scanning ranges is indicated respectively with "E11", "E12", and "E13". Incidentally, SR1, SR2, and SR3 shown in FIG. 3 are only an example. Selectable candidates for the scanning range can be displayed in the number that is settable depending on the scanning period (SR1, SR2, SR3, ..., SRn). In addition, the scanning ranges SR1, SR2, and SR3 shown in FIG. 3 have a common end E0 as one end of each of the scanning ranges (the starting point or the ending point).

The display controller 35 receives the information of one end that is input by the user using the input unit 34. The display controller 35 then specifies the position E0 of the one end that corresponds to the information of one end, as coordinates on the scanogram G. The display controller 35 then reads out the scanning ranges SR1, SR2, SR3 from the storage 13. After that, the display controller 35 displays the scanning ranges SR1, SR2, SR3 as selectable candidates over the scanogram G with the position E0 of the one end being specified as the starting point.

This embodiment is arranged such that the length of each of the scanning ranges SR1, SR2, SR3 is not set as a consecutive value in adjustment but is singly selected from the preset values (lengths), which change discretely. In other words, each of the scanning ranges SR1, SR2, SR3 has a respective fixed length. The display controller 35, upon receiving the information of the position E0 of one end, which has been specified, calculates the positions of the other ends of the scanning ranges. For example, if the lengths of the scanning ranges SR1, SR2, SR3 are represented respectively with L1, L2, L3, then the display controller 35 calculates the positions of the respective other ends as E11(=E0+L1), E12(=E0+L2), E13 (=E0+L3). In other words, the increments between the lengths L1-L3 are discrete in correspondence with the respective scanning ranges SR1-SR3, which have been calculated with the above-mentioned exemplified expressions. The positions E11, E12, E13 of the other ends are, therefore, of discrete values.

The display controller 35 uses the position E0 of the one end, which has been specified, and the positions E11, E12, E13 of the other ends which have been calculated and cause the display 33 to display the respective scanning ranges SR1, SR2, SR3, each of which is represented in a rectangle. Incidentally, FIG. 3 shows an example of scanning ranges SR1, SR2, SR3 that are displayed with discrete values as the positions E11, E12, E13 of the other ends. The method of setting up a scanning range shown in FIG. 3 is effective if the position E0 of one end of the scanning range is assumed as reference (stationary). In other words, the position E0 of one end that corresponds to either the starting point or the ending point of the scanning range is fixed in the method of setting up a scanning range shown in FIG. 3. On the other hand, the position of the other end with respect to the position E0 of the one end can be changed by the user selecting any of the selectable candidates SR1, SR2, SR3, ..., SRn as the scanning range. In the example shown in FIG. 3, therefore, while the position of one end of the scanning range is fixed, the position of the opposite end can be easily modified by the user simply selecting one among candidates discretely determined for the scanning range.

In the above-mentioned method of setting up a scanning range as shown in FIG. 3, the display controller 35 presents a setup screen for scanning range selection so that the user can set a scanning range by using the input unit 34. For example, the display controller 35 causes the display 33 to display a setup screen that makes use of a scanogram G. For this case, therefore, the X-ray CT system should acquire a scanogram (or scout image) before starting a shuttle scanning session. For example, the display controller 35 moves a mouse pointer (cursor) over the scanogram G displayed on the display 33 in correspondence with the movement of the mouse being operated by the user. The control unit acquires the coordinates of the clicked position on the setup screen when the user makes a mouse click while the mouse pointer is in a predetermined position on the setup screen. The control unit then specifies the coordinates on the setup screen as the position of one end of the scanning range. For example, the control unit relates the coordinates specified as the position of one end of the scanning range to a corresponding position in real space, based on the relationship between coordinates on the scanogram and positions in real space specified with respect to the top plate 22, and so on. Incidentally, the specification of the position of one end of the scanning range may be executed by the user inputting a numerical value with the keyboard.

After that, the display controller 35 selects one scanning range from a plurality of scanning ranges SR1, SR2, SR3 in response to the operation by the user with the input unit 34.

In the above-mentioned arrangement, the display controller 35 specifies the position E0 of one end of the scanning range as coordinates on the scanogram G, fixes the position E0 and calculates respective scanning ranges SR1, SR2 and SR3, to be displayed on a setup screen. However, the present embodiment is not limited to this. For example, if the user operates, with the input unit 34, to move the one end E0 of the scanning range, then the display controller 35 acquires coordinates for the position E0 of the one end after the movement. Furthermore, the display controller 35 calculates coordinates for each of the positions E11, E12 and E13 of the other ends that are distanced by the lengths L1, L2 and L3 from the coordinates of the position E0 of the one end after the movement. Furthermore, the display controller 35 displays, on the setup screen, the position E0 of the one end after the movement and the positions E11, E12 and E13 of the other ends, which are separated from the position of the one end by the lengths L1, L2 and L3, based on the respective sets of coordinates that have been calculated. In other words, on the setup screen, the one end E0 and the other ends E11, E12 and E13 defining the scanning ranges are moved and displayed together in correspondence with the operation.

Likewise, if the user operates with the input unit 34 to move the other end E13 of a scanning range, then the display controller 35 acquires coordinates for the position E13 of the other end after the movement. Then, the display controller 35 calculates coordinates for the position E0 of the one end, which is positioned away by the length L3 from the coordinates of the position E13 of the other end. After that, the display controller 35 displays, on the setup screen, the position E13 of the other end after the movement and the position E0 of the one end, which is distanced therefrom by the length L3, based on the respective sets of coordinates that have been calculated. The display controller, then, calculates coordinates for the positions E11 and E12 of the other ends that are distanced respectively by the lengths L1 and L2 from the coordinates of the position E0 of the one end after the movement. Furthermore, the display controller 35 displays on the setup screen the positions E11 and E12 of the other ends after the movement, based on the respective sets of coordinates that have been calculated. In other words, on the setup screen, the one end E0 and the other ends E11, E12 and E13 of the scanning ranges are moved and displayed together in correspondence with the operation by the user. Incidentally, for the case where the other end E11 or E12 of another scanning range, instead of the above-mentioned range with E13, is moved, the operation is the same.

In the arrangement where one end and the other end of a scanning range are moved together, which has been described above, only the lengths L1, L2 and L3 of the respective scanning ranges SR1, SR2 and SR3 are of discrete values. In other words, the user can modify, as serial values, the position E0 of one end of each of the scanning ranges SR1, SR2 and SR3 and the positions E11, E12 and E13 of the other ends. This arrangement is effective for a case where the one end E0 and the other ends may be moved together without fixation of the one end E0 for the scanning ranges.

(Contrastive Example)

Figure 4:
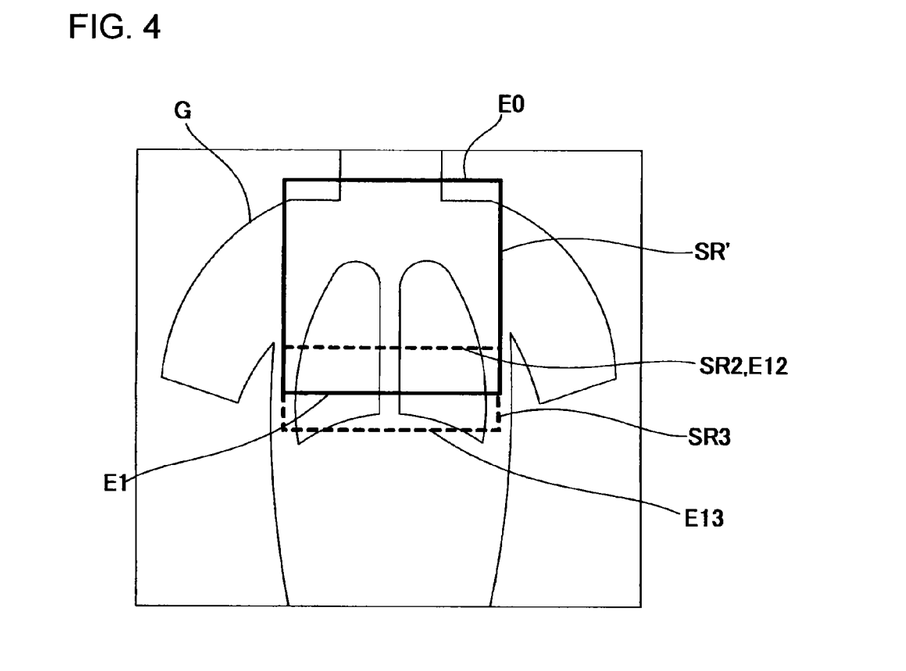
FIG. 4 is a drawing showing scanning ranges that are indicated over a scanogram as a contrastive example.

Now, a technique as a contrastive example is described with reference to FIG. 4, which is a drawing showing a scanning range that is displayed over a scanogram as a contrastive example. In FIG. 4, the scanogram is designated with "G"; the scanning range set by the technique of the contrastive example is designated with "SR'"; the starting point of the scanning range is designated with "E0"; and the ending point of the scanning range is designated with "E1".

In addition, FIG. 4 shows other scanning ranges SR2, SR3 that have been calculated and displayed according to the present embodiment. In FIG. 4, the position E12 of one end of scanning range SR2, and the position E13 of one end of scanning range SR3 are indicated respectively with dashed lines. For example, scanning range SR2 is the range when the integer n is 2 (n=2), and scanning range SR3 is the range when the integer n is 3 (n=3).

The following expression (6) expresses relations in length [mm] between the scanning ranges SR2, SR3, SR'.

$$SR2 < SR' < SR3 \quad (6)$$

Furthermore, if the length [sec] of the duration SS for scanning range SR2 is represented by "T2", and if the length of the duration SS for scanning range SR3 is represented with "T3", then the relation between T2 and T3 is expressed by the following expression (7). Incidentally, as mentioned above, the duration SS is the time required for the top plate 22 to make one reciprocating movement within each of the scanning ranges, which have been set up.

$$T2 < T3 \quad (7)$$

Incidentally, in the description of the contrastive example, the position E0 of one end of the scanning range is fixed for the display controller 35 to display a plurality of scanning ranges SR'.

In the contrastive example, what is different from the present embodiment is that the setup of the scanning range SR' can be modified with serial values. In other words, the scanning range SR' is not set with a discrete value. The display controller 35, therefore, displays the other end E1 of the scanning range SR' continually movable in correspondence with the setup operation being executed by the user. In other words, the position E1 of the other end of the scanning range SR' is changed and set with serial values.

The scanning range SR' in the contrastive example can be continually changed before being set at a desired point. Consequently, it is necessary that the waiting time PS include a time for making tracking agreement between the consecutive IN actions, and likewise, it is necessary that the waiting time PS include a time for making tracking agreement between the consecutive OUT actions. In other words, there is an increase in the duration for the top plate to make one reciprocating movement in the shuttle scanning. As a result, the interval between the consecutive times for acquiring respective data sets that correspond to the consecutive IN actions is made longer by the time required for making tracking agreement. Likewise, the interval between the consecutive times for acquiring respective data sets that correspond to the consecutive OUT actions is made longer by the time required for making tracking agreement. This may result in a reduction in the accuracy of the analysis conducted by using the differential images.

As described above, in the contrastive example, the waiting time PS includes the time for making precise tracking agreement, so the duration SS is longer by this time. By contrast, in the present embodiment, the waiting time PS does not include the time for making tracking agreement, so the duration SS is shorter by this reason. As a result, the scanning range can be extended in the present embodiment by the time difference between the duration SS of the contrastive example and that of the present embodiment. In other words, according to the present embodiment, this time difference can be allocated to expansion of the scanning range. For example, according to the present embodiment, for the same duration SS (=T3), scanning can be done over scanning range SR3, which is broader than scanning range SR'.

On the other hand, in a case where the object the user desires to scan is wholly included within scanning range SR2, this scanning range SR2 is a sufficient range, but scanning range SR', which is broader than this range, includes extra range. In this case, since the duration SS for executing scanning over scanning range SR2 is shorter than the duration required over scanning range SR' (T2<T3), the duration SS in general can be also short in other cases.

(Variant Embodiments)

Figure 5:
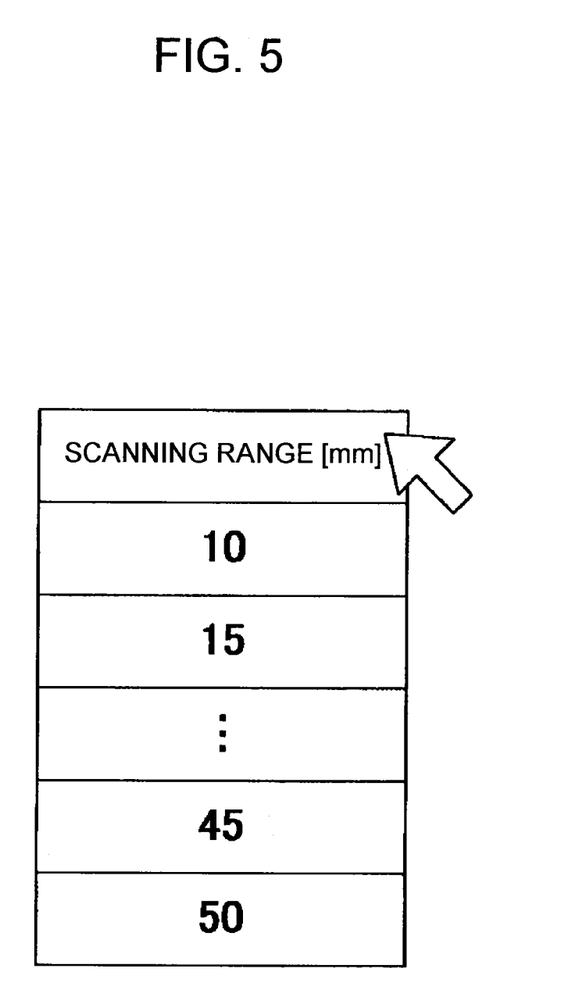
FIG. 5 is a drawing showing a plurality of scanning ranges that are displayed as selectable, as a variant embodiment.

Now, a variant embodiment is described with reference to FIG. 5, which is a drawing showing a plurality of scanning ranges that are displayed as selectable in the variant embodiment.

In the above-mentioned arrangement, the display controller 35 reads out scanning ranges SR1, SR2 and SR3 from the storage 13 and displays them as selectable items over a scanogram G, with the position E0 of one end specified for each of the scanning ranges SR1, SR2 and SR3 as the starting point. The present embodiment is, however, not restricted to this, and it can be arranged, for example, in the following way.

The display controller 35 causes the display 33 to display a pull-down menu to let the user select a scanning range. For example, the display controller 35 displays the text "Scanning Ranges" at one end of the display area of the pull-down menu and displays a plurality of scanning ranges SR1, SR2, SR3, . . . , SRn in alignment from the side of the text description to the other end side of the pull-down menu. As an example, if the user executes, with the input unit 34, the operation of pulling down the display area "Scanning Range" of the pull-down menu, then the display controller 35 displays, in alignment, selectable candidates representing a plurality of scanning ranges, which have been hidden until this point. After receiving the selection of a candidate made by the user with the input unit 34, which is an operation of assigning a scanning range, the display controller 35 reads out from the storage 13 the information of the scanning range that corresponds to the selection. Furthermore, as the selectable candidates for the scanning range being displayed on the pull-down menu, the lengths [mm] of respective scanning ranges may be displayed as shown in FIG. 5, instead of scanning ranges SR1 , SR2 , SR3 , . . . , SRn. For example, in this case, the pull-down menu shows numerical values, for example, "10", "15", . . . , "45", "50" as shown in FIG. 5, which are the lengths [mm] of respective scanning ranges. In this example, the selectable candidates for the scanning range are shown as discrete values with an increment of 5 [mm].

(Sequence of Actions)

Now, actions taken by the X-ray CT system for calculating a scanning range and displaying it are described with reference to FIG. 6, which is a flowchart showing a flow of actions taken by the X-ray CT system from the calculation of a scanning range to image reconstruction.

Figure 6:
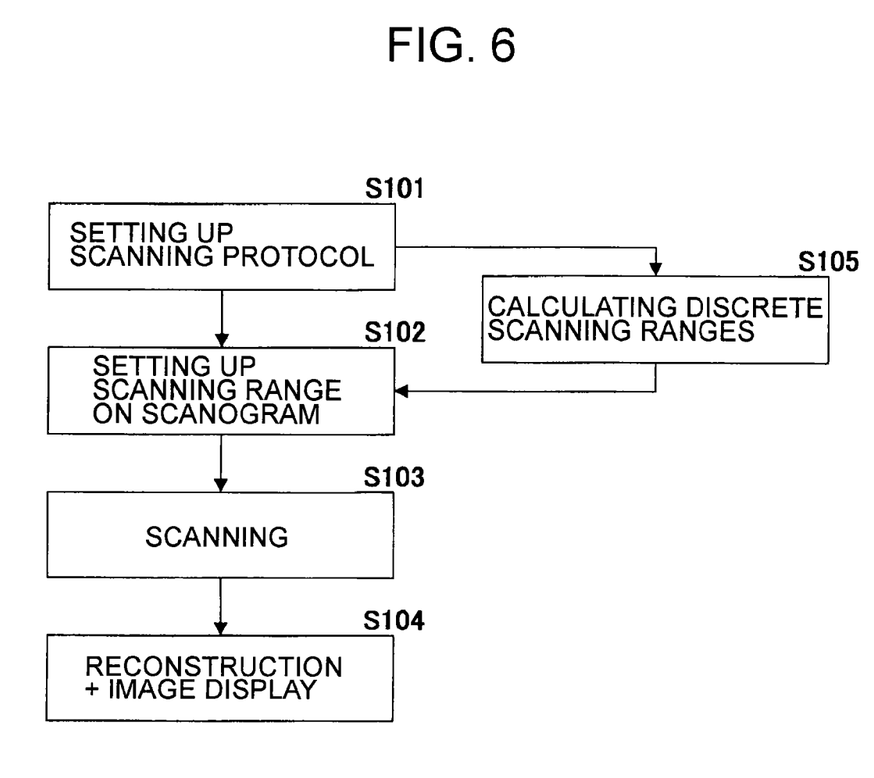
FIG. 6 is a flowchart showing a flow of actions taken by the X-ray CT system after the calculation of the scanning range until the image reconstruction.

As shown in FIG. 6, upon the activation of the X-ray CT system by the user, a scanning protocol is set up (step S101). Incidentally, a scanogram of the subject P has been acquired in advance and is stored in the storage 13 or in another storage device.

In the setting up of the protocol, the user inputs, through the interface 32, such basic conditions as the tube voltage of the X-ray tube, which is included in the X-ray radiator 21, the X-ray dosage to be radiated by the X-ray tube, the revolution period (revolution speed) of the X-ray radiator 21, and so on. Furthermore, in the setting up of the protocol, the user may input the duration (period) for the top-plate moving unit 15 to drive the top plate 22 to make one reciprocating movement.

At this instant, the X-ray CT system according to the present embodiment is preset to allow the duration for one reciprocating movement of the top plate 22 to be selected only as an integral multiple of the revolution period of the X-ray radiator 21 in the setting up of the protocol. For example, the respective scanning ranges SR displayed on a pull-down menu in the setting up of the protocol are determined such that the duration for the top plate 22 to make a reciprocating movement is an integral multiple of the revolution period of the X-ray radiator 21. Instead, as a way of setting up the protocol on the X-ray CT system, the setup screen may be arranged to make the user input a duration as has been described above. In such a case, the setup screen is so arranged that the user inputs a numerical value for the duration required for the top plate 22 to make a reciprocating movement, instead of choosing a selectable. However, it is necessary that the control unit or display controller 35 compare the numerical value for the duration input by the user on the setup screen to the revolution period of the X-ray radiator 21. As a result of the comparison, if the input duration does not correspond to an integral multiple of the revolution period, then the display controller 35 reads out the information for displaying a warning message from the storage (not shown) and causes the display 33 to display an appropriate warning message. As an example, the warning message is displayed as the text message "Please input the duration as an integral multiple of the revolution period (speed)". Incidentally, this warning is not restricted to text messages, so it may be a voice message.

Furthermore, the setup screen for setting up the protocol may be arranged to make the user input numerical values as a scanning range. This setup screen is arranged to allow the user to input a starting point and an ending point for defining a scanning range. In this arrangement, the control unit compares the duration that has been calculated from the length of the scanning range input to the revolution period of the X-ray radiator 21. The length of the scanning range is the length in the rostrocaudal direction of the subject or in the direction of movement of the top plate. In the comparison, the control unit determines whether or not the duration that has been calculated from the length of the input scanning range corresponds to an integral multiple of the revolution period of the X-ray radiator 21. If the determination by the control unit results in that the duration does not correspond to an integral multiple of the revolution period, then the X-ray CT system outputs a warning in the same way as the above-mentioned example for the input of a duration.

As another example, when the user inputs a starting point and an ending point for a scanning range on the setup screen for setting up the protocol, no constraints may be provided for the input of a starting point while providing some constraints for the input of an ending point. Such constraints may be any constraints that provide limitation, for example, rounding up, rounding down, or rounding off of the input value to the nearest integral multiple.

Then, the display controller 35 calculates coordinates for the scanning range on the scanogram and causes the display 33 to display it (step S102).

Before or in parallel to this step, the display controller 35 calculates discrete scanning ranges (step S105). In other words, the display controller 35 reads out a plurality of scanning ranges from the storage 13 and, on the basis of the position E0 of one end of the respective scanning ranges SR1 , SR2 and SR3 on the scanogram, calculates the positions E11, E12, and E13 of the other ends. The display controller 35 causes the display 33 to display the scanning ranges SR1 , SR2 and SR3 , based on the respective positions E11, E12, and E13 of the other ends, which have been calculated. When the user makes an operation to select one of the displayed scanning ranges, the control unit sets the selected scanning range as the scanning range for the shuttle scanning. There is a discrete increment between the positions E11, E12, and E13 of the other ends of the scanning ranges, which are opposite to the position E0 of the one end.

The control unit, then, controls the top-plate moving unit 15 to drive the top plate 22, based on the scanning range that has been set as described above, for execution of the scanning (step S103).

During the scanning, the control unit detects X-rays that have passed through the subject P and executes reconstruction-processing on the projection data. Tomographic images are generated by the reconstruction-processing, and the display controller 35 causes the display 33 to display the tomographic images (step S104).

Now, the description concerns the operation and effects of the present embodiment, which has been described above.

The present embodiment and its variant embodiment, which have been described above, are configured such that scanning ranges are discretely provided in the setting up of a scanning range for shuttle scanning. According to such configuration, it is not necessary to include a time for making precise tracking agreement in the waiting time after the top plate 22 has made one reciprocating movement and before it starts another reciprocating movement in shuttle scanning. In other words, when differential images are generated from between the data sets that are achieved for the IN actions in shuttle scanning, even though a time for making tracking agreement between the IN actions is not included between each OUT action and the immediately following IN action, there is always tracking agreement between the consecutive IN actions. Likewise, when differential images are generated from between the data sets achieved for the OUT actions in shuttle scanning, even without a time intentionally secured for making tracking agreement, there is always tracking agreement between the consecutive OUT actions.

It is, therefore, possible that the scanning period for data acquisition over the set scanning range be comparatively shortened to make a reduction in radiation dose. As a result, it is also possible that the interval be shortened between the times for data acquisition with the IN actions in shuttle scanning and between the times for data acquisition with the OUT actions. This can result in an improvement in the accuracy of the analysis conducted by using the differential images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

DESCRIPTIONS OF NUMBERED PARTS

10, X-ray CT system;
11, System controller;
12, Scanning controller;
13, Storage;
14, Table;
15, Top-plate moving unit;
16, Rotary moving unit;
17, X-ray controller;
19, High voltage generator;
21, X-ray radiator;
22, Top plate;
23, X-ray detector;
25, Rotary mechanism;
27, Data acquisition system;
31, Reconstruction processor;
32, Interface;
33, Display;
34, Input unit;
35, Display controller.

What is claimed is:

1. An X-ray CT system comprising:
a top plate on which a subject is placed;
a top-plate moving unit configured to displace the top plate to reciprocate in a direction from a predetermined starting point to a predetermined ending point and in the direction from the ending point to the starting point;
a rotary moving unit configured to drive an X-ray radiator, which radiates X-rays, to revolve around the subject;
a data acquisition system configured to detect X-rays that have passed through the subject and to gather projection data; and
a control unit configured to control at least the top-plate moving unit in such a way that, during a scanning with X-rays, while the projection data are gathered with the top plate being driven to make one reciprocating movement including moving from the starting point to the ending point and moving from the ending point to the starting point and with the X-ray radiator being driven to make revolving movement, the duration required for the top plate to make the one reciprocating movement is made an integer multiple of the revolution period of the revolving movement of the X-ray radiator.

2. An X-ray CT system according to claim 1, further comprising:
a storage configured to store a plurality of scanning ranges that are so predetermined that the duration for each of the scanning ranges is an integer multiple of the revolution period, the scanning ranges being distances from the starting point to the ending point;
an input unit;
a display; and
an interface configured to include a display controller that controls the display;
wherein
the display controller causes the display to display as selectable the scanning ranges stored in the storage.

3. An X-ray CT system according to claim 2, wherein
the display controller, upon receiving information of one end input with the input unit, specifies a position for the one end as coordinates on a scanogram of the subject; and
the display controller displays each of the scanning ranges as selectable over the scanogram, with the position of the specified one end being the starting point of each of the scanning ranges.

4. An X-ray CT system according to claim 2, wherein
the control unit, based on the selection of a scanning range, is configured to calculate an acceleration time during which the top plate is moved by acceleration, a constant speed time during which the top plate is being translated at a constant speed, and a deceleration time during which the top plate is moved by deceleration, these times being included in the duration for the scanning range;
the control unit also calculates a waiting time, during which the top plate is stationary; and
the control unit controls at least one of the top-plate moving unit and the X-ray radiator, based on the acceleration time, the constant speed time, the deceleration time, and the waiting time, which have been calculated.

5. An X-ray CT system according to claim 4, further comprising a table for storing the acceleration time, the constant speed time, the deceleration time, and the waiting time in correspondence with the scanning range.

6. An X-ray CT system according to claim 3, wherein
the control unit, based on the selection of a scanning range, is configured to calculate an acceleration time during which the top plate is moved by acceleration, a constant speed time during which the top plate is being translated at a constant speed, and a deceleration time during which the top plate is moved by deceleration, these times being included in the duration for the scanning range;
the control unit also calculates a waiting time, during which the top plate is stationary; and
the control unit controls at least one of the top-plate moving unit and the X-ray radiator, based on the acceleration time, the constant speed time, the deceleration time, and the waiting time, which have been calculated.

7. An X-ray CT system according to claim 6, further comprising a table for storing the acceleration time, the constant speed time, the deceleration time, and the waiting time in correspondence with the scanning range.

8. An X-ray CT system according to claim 1, wherein the reciprocating movement includes a time where the top plate is stopped after it has been moved from the starting point to the ending point and before it is to be moved from the ending point to the starting point.

9. An X-ray CT system according to claim 1, wherein the reciprocating movement includes a time where the top plate is stopped after it has been moved from the ending point to the starting point and before it is to be moved from the starting point to the ending point in a next reciprocating movement.

10. An X-ray CT system according to claim 1, wherein the reciprocating movement includes a first time where the top plate is stopped after it has been moved from the ending point to the starting point and before it is to be moved from the starting point in a next reciprocating movement, and the reciprocating movement includes a second time where the top plate is stopped after it has been moved from the ending point to the starting point and before it is to be moved from the starting point to the ending point in a next reciprocating movement.

11. An X-ray CT system according to claim 1, wherein the reciprocating movement includes two acceleration periods.

12. An X-ray CT system according to claim 1, wherein the reciprocating movement includes two deceleration periods.

13. An X-ray CT system according to claim 1, wherein the reciprocating movement includes two constant velocity periods.

14. An X-ray CT system according to claim 1, wherein the reciprocating movement includes a stationary period.

15. An X-ray CT system according to claim 1, wherein the reciprocating movement includes two stationary periods.

16. An X-ray CT system according to claim 1, wherein the reciprocating movement includes two acceleration periods, two deceleration periods, and two constant velocity periods.

17. An X-ray CT system according to claim 16, wherein the reciprocating movement includes two stationary periods.

18. An X-ray CT system according to claim 1, wherein the scanning with the X-rays is bounded by starting point and the ending point, inclusive.

19. An X-ray CT system according to claim 18, wherein the reciprocating movement includes only positions of the top plate within the scanning range, inclusive.

* * * * *